(12) United States Patent
Meng

(10) Patent No.: US 10,513,495 B2
(45) Date of Patent: Dec. 24, 2019

(54) POLYMORPH OF PIMAVANSERIN TARTRATE AND PREPARATION METHOD THEREOF AND USE OF SAME

(71) Applicant: SHANGHAI BEGREAT PHARMATECH, Shanghai (CN)

(72) Inventor: Xiaoming Meng, Tianjin (CN)

(73) Assignee: SHANGHAI BEGREAT PHARMATECH, Shanghai (CN)

( * ) Notice: Subject to any disclaimer, the term of this patent is extended or adjusted under 35 U.S.C. 154(b) by 0 days.

(21) Appl. No.: 16/194,486

(22) Filed: Nov. 19, 2018

(65) Prior Publication Data

US 2019/0084935 A1    Mar. 21, 2019

Related U.S. Application Data

(63) Continuation of application No. PCT/CN2017/084983, filed on May 19, 2017.

(30) Foreign Application Priority Data

May 19, 2016 (CN) .......................... 2016 1 0347779

(51) Int. Cl.
    *C07D 211/58* (2006.01)
    *A61P 25/16* (2006.01)
    *A61P 7/02* (2006.01)
    *A61P 25/28* (2006.01)

(52) U.S. Cl.
    CPC .............. *C07D 211/58* (2013.01); *A61P 7/02* (2018.01); *A61P 25/16* (2018.01); *A61P 25/28* (2018.01); *C07B 2200/13* (2013.01)

(58) Field of Classification Search
    CPC .......... C07D 211/58; A61P 25/28; A61P 7/02; A61P 25/16; C07C 59/255; C07C 51/43; A61K 31/4468; C07B 2200/13
    See application file for complete search history.

(56) References Cited

U.S. PATENT DOCUMENTS

| 10,343,993 B2 * | 7/2019 | Biljan |
| 2006/0106063 A1 | 5/2006 | Thygesen et al. |

FOREIGN PATENT DOCUMENTS

| CN | 104961671 A | 10/2015 |
| CN | 104961672 A | 10/2015 |
| CN | 105523993 A | 4/2016 |
| WO | 2006036874 A1 | 4/2006 |
| WO | 2006037043 A1 | 4/2006 |
| WO | 2008144326 A2 | 11/2008 |

OTHER PUBLICATIONS

International Search Report in PCT/CN2017/084983 dated Jan. 3, 2018, 3 pages.

* cited by examiner

Primary Examiner — John M Mauro
(74) Attorney, Agent, or Firm — Metis IP LLC

(57) ABSTRACT

A polymorph III of N-(4-fluorobenzyl)-N-(1-methylpiperidin-4-yl)-N'-[4-(2-methylpropoxy)phenylmethyl]urea tartrate, a preparation method therefor, and a medicinal use. Compared to the existing crystalline forms, the new crystalline form has clear advantages with respect to solubility, stability and the preparation process.

9 Claims, 1 Drawing Sheet

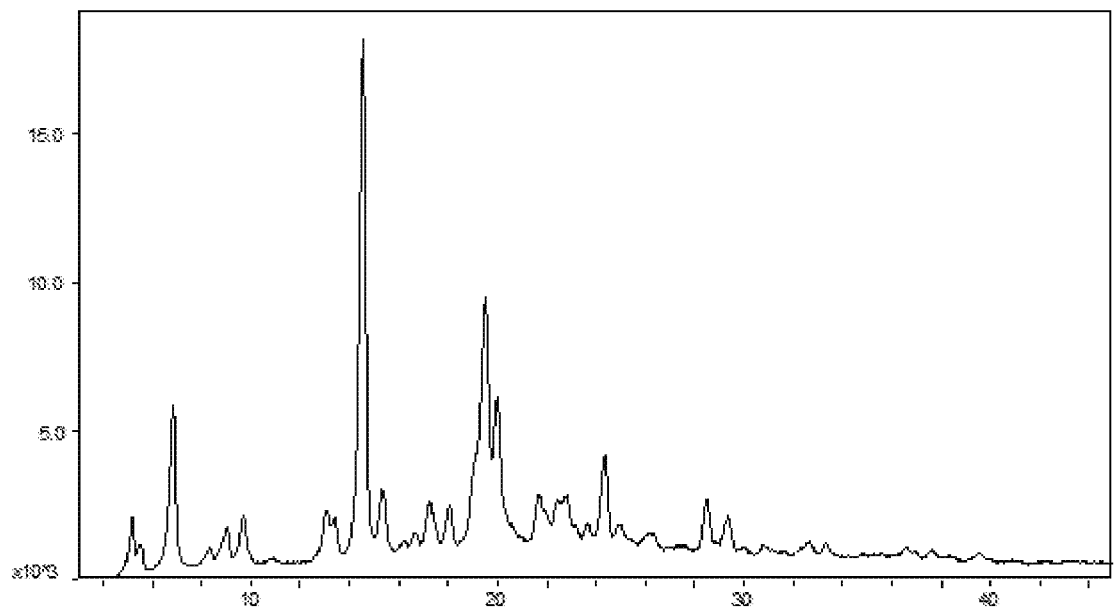

POLYMORPH OF PIMAVANSERIN TARTRATE AND PREPARATION METHOD THEREOF AND USE OF SAME

CROSS-REFERENCE TO RELATED APPLICATIONS

This application is a continuation of International Application No. PCT/CN2017/084983 filed on May 19, 2017, which claims priority to Chinese Application No. 201610347779.3, filed on May 19, 2016. The above-referenced applications are incorporated herein by reference in their entirety.

TECHNICAL FIELD

The present invention relates to novel crystals of N-(4-fluorobenzyl)-N-(1-methylpiperidin-4-yl)-N'-[4-(2-methylpropoxy)phenylmethyl]urea tartrate form III and its preparation method and use.

BACKGROUND

More than 10 million people worldwide suffer from Parkinson's disease, and more than 50% of them ill suffer from mental disorders (mainly hallucinations and illusions). Mental symptoms are very common in patients with Parkinson's disease, that is very distressed to take care of them. Mental illness is the main driving factor for Parkinson's patients to be sent to sanatoriums, which greatly increases the risk of death. At present, the only alternative treatment is dopamine antagonists such as clozapine and quetiapine, which may aggravate motor symptoms, accelerate cognitive impairment, increase the risk of stroke and even endanger life even if they are used for a short time.

Compound 1, Pimavanserin tartrate, (N-(4-fluorobenzyl)-N-(1-methylpiperidin-4-yl)-N'-[4-(2-methylpropoxy)phenylmethyl]urea tartrate) is a drug approved by the US FDA under the trade name NUPLAZID. The drug was developed by Acadia Pharmaceuticals. It is suitable for the treatment of hallucinations and delusions associated with Parkinson's disease. Pimavanserine works by blocking the serotonin 2A receptor on the neocortex, which is the brain region responsible for sensory, awake thinking and language, as well as visual hallucinations and illusions. The discovery and application of Pimavanserine opens up new avenues for the treatment of Parkinson's disease. Because of its potentially good safety, pimavanserine may help treat patients with Parkinson's disease and mild psychiatric symptoms, help prevent more troublesome symptoms, and target psychiatric symptoms of other diseases, such as Alzheimer's disease.

Pimavanserin has potential for the treatment of diseases such as: psychosis, schizophrenia, schizoaffective disorder, mania, psychosis, affective disorder, dementia, anxiety, sleep disorders, appetite disorders, double Phase-related mental disorders, psychosis secondary to hypertension, migraine, vasospasm and ischemia, motor convulsions, tremors, psychomotor retardation, bradykinesia and psychotic pain, Parkinson's, Huntington's disease, Alzheimer's Disease, spinal cerebellar atrophy, Tourette's syndrome, Friedreich's ataxia, Machado-Joseph's disease, Lewy body dementia, progressive supranuclear palsy and frontotemporal dementia, myoclonus, or tremor, myocardial infarction, thrombotic or ischemic stroke, idiopathic and thrombotic thrombocytopenic purpura, peripheral vascular disease, and Raynaud's disease.

Pimavanserin has a molecular formula of $C_{25}H_{34}FN_3O_2$ and a molecular weight of 427.5. The chemical structure of Pimavanserin is as follows:

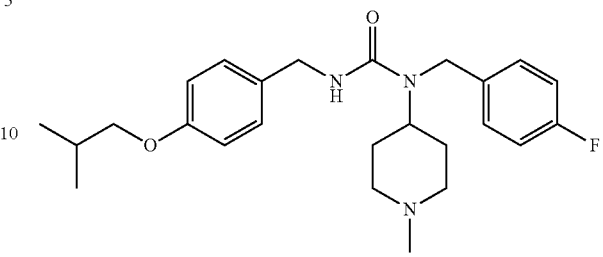

Chemical raw materials of active pharmaceutical ingredients (API) must have good purity, stability, physical and chemical properties and operability. These properties are related to the crystalline form of the drug, and different crystal forms have different physical and chemical properties. The purpose of improving the stability of the drug preservation and the efficacy of the drug, it is necessary to make the raw API into crystal form.

A drug may exist in a plurality of crystalline forms, and different crystal forms of the same drug may have different dissolution and absorption in the body, thereby affecting the dissolution and release of the formulation.

The optimal crystalline form can be discovered by thoroughly studying of the polymorphism of the compound. The optimal crystalline form is crucial to the efficacy of the drug and the formulation process which is based on the characteristics of the crystalline form, thereby effectively ensuring the equivalence of the drug batch to batch.

Drug powder flowability is also an important factor throughout the pharmaceutical formulation process. When the powder or the capsule formulation was prepared by directly mixing and filling, components are difficult to mix uniformly and affect the exact content of the drug product due to poor powder flowability. In the process of compressing or filling of granules, tablets, capsules, etc., the particles with poor flowability tend to make the surface rough of drug product or not easy to dispersible of the drug which lead to inconvenient for patients to take. Poor flowability of the drug powder also affects the smooth process and increase the cost of the drug product preparation. In the application of external powder topical formulation, the powder with poor powder flowability will lead to unevenly coated of the drug resulting in excessive or excessive topical application, which finally affecting the efficacy of the drug. In the storage and transportation of the preparation, the formulation made of the powder with poor fluidity is more susceptible to the influence of ambient temperature, humidity, pressure, mechanical force and the like to reduce the stability and effectiveness of the drug.

Angle of repose is adopted widely to evaluate the powder flowability. When the angle of repose of the powder is less than or equal to 30 degrees, it means the flowability of this powder is good. While in case, 40 degrees or less of the powder angle of repose, this powder can satisfy the demand for fluidity in the production process. When the angle of repose of the powder is more than 40 degrees, it means the very poor flowability of the drug powder which may cause the troubles above mentioned during the drug manufacturing process.

SUMMARY

The main object of the present invention is to provide N-(4-fluorobenzyl)-N-(1-methylpiperidin-4-yl)-N'-[4-(2- methylpropoxy)phenylmethyl]urea tartrate (Pimavanserin tartrate) new crystalline form III, and process for its preparation and a medicinal use.

A crystalline form of N-(4-fluorobenzyl)-N-(1-methylpiperidin-4-yl)-N'-[4-(2-methylpropoxy)phenylmethyl]urea tartrate designated as crystal form III, having an X-ray powder diffraction pattern comprising diffraction peaks at at least one 2θ value of: 14.6±0.2, 19.5±0.2, 6.9±0.2, 20.0±0.2 24.4±0.2. Preferably, wherein the X-ray powder diffraction pattern further comprises diffraction peaks at 2θ values: 19.1±0.2, 5.2±0.2, 15.3±0.2 28.5±0.2, 13.1±0.2, 9.7±0.2. Preferably, wherein the X-ray powder diffraction pattern further comprises diffraction peaks at 2θ values: 9.0±0.2, 5.6±0.2, 29.4±0.2, 23.7±0.2, 25.0±0.2, 26.3±0.2. Preferably, wherein the X-ray powder diffraction pattern further comprises diffraction peaks at 2θ values: 32.6±0.2, 8.3±0.2, 16.7±0.2, 33.3±0.2, 36.6±0.2, 30.8±0.2. More preferably, wherein the X-ray powder diffraction pattern further comprises diffraction peaks at 2θ values: 39.6±0.2, 16.2±0.2, 37.6±0.2, 10.9±0.2, 27.5±0.2, 37.0±0.2.

A process for the preparation of N-(4-fluorobenzyl)-N-(1-methylpiperidin-4-yl)-N'-[4-(2-methylpropoxy)phenylmethyl]urea tartrate crystal form III comprising:
(i) dissolving N-(4-fluorobenzyl)-N-(1-methylpipedin-4-yl)-N'-[4-(2-methylpropoxy)phenylmethyl]urea tartrate free base in an organic solution;
(ii) adding tartaric acid in a molar amount no less than the free base into the solution prepared in the step (i) to precipitate a N-(4-fluorobenzyl)-N-(1-methylpiperidin-4-yl)-N'-[4-(2-methylpropoxy)phenylmethyl]urea tartrate salt; and
(iii) obtaining N-(4-fluorobenzyl)-N-(1-methylpiperidin-4-yl)-N'[4-(2-methylpropoxy)phenylmethyl]urea tartrate crystal form III of after liquid-solid separation.

A pharmaceutical composition may comprise the crystal form III of N-(4-fluorobenzyl)-N-(1-methylpiperidin-4-yl)-N'-[4-(2-methylpropoxy)phenylmethyl]urea tartrate as an active ingredient.

A use of N-(4-fluorobenzyl)-N-(1-methylpiperidin-4-yl)-N'-[4-(2-methylpropoxy)phenylmethyl]urea tartrate crystal form and a pharmaceutical composition thereof is for the treatment of a dopamine receptor-related disease including mental illness, neurodegenerative diseases, dyskinesia, dystonia and thrombosis.

The dopamine receptor-related disease may further include psychosis, schizophrenia, schizoaffective disorder, mania, psychotic depression, affective disorder, dementia, anxiety, sleep disorder, appetite disorder, bipolar disorder, psychosis secondary to hypertension, migraine, vasospasm and ischemia, motor convulsions, tremors, psychomotor retardation, bradykinesia and psychotic pain, Parkinson's disease, Huntington's disease, Alzheimer's disease, spinocerebellar atrophy, Tourette Syndrome, Friedreich Ataxia, Machado-Joseph disease, Lewy body dementia, progressive supranuclear palsy and frontotemporal dementia, myoclonus, or tremor, myocardial infarction, thrombosis Sexual or ischemic stroke, idiopathic and thrombotic thrombocytopenic purpura, peripheral vascular disease, and Raynaud's disease.

The patents WO2006037043A1 disclose the crystalline forms A, B, C, D, E and crystalline form F of pimavanserin tartrate, wherein the crystalline forms D, E and F are respectively pimavanserin tartrate isopropanol solvate, Tert-butyl ether solvate and tetrahydrofuran solvate which are not suitable for pharmaceutical development. Forms A, B, and C are hydrates and are suitable for pharmaceutical development. However, it has been found that the flowability of crystal forms A, B and C is poor, which affects the formulation development. Due to the poor flowability of pimavanserin drug powder in forms of A, B and C, the drug powder is hard to be blended with excipients which lead to the content uniformity and assay of the pimavanserin drug product such as capsules. When filling the pimavanserin capsules or tablets, the forms of A, B and C with poor flowability tend to make the surface rough of drug product or not easy to dispersible of the drug which lead to inconvenient for patients to take. The poor flowability of the forms of A, B and C is also affects the smooth process and increase the cost of the pimavanserin product preparation. During the storage and transportation, the formulations of the powders with poor flowability of the pimavanserin tartrate crystal forms A, B, and C are more susceptible to the effects of environmental temperature, humidity, pressure, mechanical force, etc. which lead to decrease the stability and effectiveness of pimavanserin drug prodcut. In order to solve the problem of the flowability of the pharmaceutically developable crystal forms A, B, and C, the present invention has found that the new crystal form III can significantly improve the flowability of the pimavanserin tartrate by a large number of crystal form screening work, thereby conducive to the development of pharmaceutical formulations.

BRIEF DESCRIPTION OF THE DRAWINGS

The drawing accompanying the present disclosure is an XPRD pattern of N-(4-fluorobenzyl)-N-(1-methylpiperidin-4-yl)-N'-[4-(2-methylpropoxy)phenylmethyl]urea tartrate Form III. 2θ values in unit of degree in accordance with the abscissa. The intensity of diffraction peak as ordinate.

EXAMPLES

The specific embodiments of the present invention are further described in detail below with reference to the drawings and embodiments. The following examples are intended to illustrate the invention, but are not intended to limit the scope of the invention.

The X-ray powder diffraction operation and analysis steps in this patent are as follows:

The Rigaku Ultima IV powder diffractometer was used, which was irradiated with Cu—K(R) (40 kV, 40 mA) at room temperature using a D/tex Ultra detector. The scanning range is from 3° to 45° in the 2θ interval, and the scanning speed is 20°/min.

Measurement differences associated with X-ray powder diffraction analysis results are produced by a variety of factors including: (a) errors in sample preparation (e.g., sample height), (b) instrument error, (c) calibration differences, (d) operator error (including errors that occur when determining peak position), and (e) properties of the substance (e.g., preferred orientation error). Calibration errors and sample height errors often result in displacement of all peaks in the same direction. When using a flat sampler, small differences in sample height will result in large displacements of the XRPD peak position. Systematic studies have shown that a 1 mm sample height difference can result in a 2θ peak shift of up to 10. These displacements can be identified from the X-ray diffraction pattern and can be eliminated by compensating for the displacement (using a system calibration factor for all peak position values) or recalibrating the instrument. As described above, the measurement errors from different instruments can be corrected by applying a system calibration factor to make the peak positions consistent.

Example 1

Slurry or dissolve 50 mg of N-(4-fluorobenzyl)-N-(1 methylpiperidin-4-yl)-N'-[4-(2-methylpropoxy)phenylmethyl]urea in 0.5 mL isopropanol, and then add tartaric acid at three times the molar equivalent of N-(4-fluorobenzyl)-N-(1-methylpiperidin-4-yl)-N'-[4-(2-methylpropoxy)phenylmethyl]urea to produce a precipitate. The precipitation was allowed to be stirred overnight and the N-(4-fluorobenzyl)-N-(1 ethylpiperidin-4-yl)-N'-[4-(2-methylpropoxy)phenylmethyl]urea tartrate was obtained.

In the present invention, the N-(4-fluorobenzyl)-N-(1-methylpiperidin-4-yl)-N'-[4-(2-methylpropoxy)phenylmethyl]urea tartrate form the XRPD patterns is shown in FIG. 1 and the diffraction peaks of the XRPD pattern of Form III are listed in the following table:

| 2-Theta | d(Å) | I(Height)% |
|---|---|---|
| 5.199 | 16.983 | 12.1 |
| 5.559 | 15.8849 | 6.2 |
| 6.859 | 12.8757 | 31.9 |
| 8.32 | 10.618 | 2.4 |
| 9.02 | 9.796 | 6.4 |
| 9.7 | 9.1105 | 8.9 |
| 10.881 | 8.1243 | 1.2 |
| 13.06 | 6.7733 | 9.3 |
| 13.399 | 6.6026 | 7.4 |
| 14.56 | 6.0789 | 100 |
| 15.322 | 5.7782 | 10.3 |
| 16.234 | 5.4555 | 1.3 |
| 16.659 | 5.3173 | 2.3 |
| 17.24 | 5.1391 | 8.4 |
| 18.041 | 4.9128 | 7.5 |
| 19.071 | 4.6499 | 16.5 |
| 19.5 | 4.5484 | 46.4 |
| 19.981 | 4.4401 | 27.6 |
| 21.661 | 4.0993 | 7.5 |
| 22.441 | 3.9586 | 7.2 |
| 22.819 | 3.8938 | 7.1 |
| 23.681 | 3.754 | 2.9 |
| 24.359 | 3.651 | 16.6 |
| 24.979 | 3.5618 | 2.9 |
| 26.259 | 3.391 | 2.6 |
| 27.022 | 3.297 | 0.6 |
| 27.52 | 3.2384 | 1.1 |
| 28.5 | 3.1293 | 9.4 |
| 29.36 | 3.0395 | 6 |
| 30.032 | 2.973 | 0.9 |
| 30.763 | 2.904 | 1.7 |
| 31.647 | 2.8249 | 0.7 |
| 32.642 | 2.7411 | 2.6 |
| 33.301 | 2.6883 | 2.3 |
| 34.885 | 2.5697 | 0.7 |
| 35.579 | 2.5212 | 0.7 |
| 36.601 | 2.4531 | 2.1 |
| 36.956 | 2.4304 | 1.1 |
| 37.581 | 2.3913 | 1.3 |
| 38.42 | 2.3411 | 0.6 |
| 39.56 | 2.2762 | 1.7 |
| 42.36 | 2.132 | 0.6 |

In the present invention, the N-(4-fluorobenzyl)-N-(1-methylpiperidin-4-yl)-N'-[4-(2-methylpropoxy)phenylmethyl]urea tartrate form III, the XRPD patterns is shown in FIG. 1 and the diffraction peaks of the XRPD pattern of Form III are listed in the following table:

| 2-Theta | d(Å) | I(Height)% |
|---|---|---|
| 5.359 | 16.4771 | 2 |
| 6.76 | 13.065 | 38.7 |
| 8.64 | 10.2261 | 2.7 |
| 9.62 | 9.1861 | 9.4 |
| 11.386 | 7.7649 | 1.1 |
| 12.999 | 6.8048 | 6.8 |
| 13.319 | 6.6424 | 10 |
| 14.162 | 6.2485 | 12.1 |
| 14.498 | 6.1043 | 59.1 |
| 15.279 | 5.7942 | 9.7 |
| 15.9 | 5.5693 | 1.4 |
| 16.124 | 5.4925 | 2.3 |
| 16.458 | 5.3817 | 3.8 |
| 17.342 | 5.1093 | 7.4 |
| 17.96 | 4.9347 | 7.6 |
| 18.655 | 4.7525 | 8.4 |
| 19.461 | 4.5575 | 29.2 |
| 19.919 | 4.4537 | 100 |
| 20.418 | 4.3459 | 1.8 |
| 21.039 | 4.219 | 5.3 |
| 21.656 | 4.1002 | 23.3 |
| 22.039 | 4.0298 | 7.9 |
| 22.579 | 3.9348 | 24.3 |
| 22.998 | 3.8639 | 3.2 |
| 23.619 | 3.7638 | 25.1 |
| 24.28 | 3.6627 | 16.5 |
| 25.656 | 3.4693 | 3.5 |
| 26.078 | 3.4141 | 6.3 |
| 26.538 | 3.356 | 3 |
| 27.018 | 3.2974 | 3.6 |
| 27.398 | 3.2525 | 2 |
| 27.801 | 3.2064 | 4.1 |
| 28.441 | 3.1356 | 10.9 |
| 28.721 | 3.1057 | 6.8 |
| 29.161 | 3.0598 | 6.5 |
| 30 | 2.9761 | 3.5 |
| 30.799 | 2.9007 | 8.1 |
| 31.139 | 2.8698 | 4.4 |
| 32.241 | 2.7742 | 3.6 |
| 32.7 | 2.7363 | 6.8 |
| 33.238 | 2.6932 | 3.4 |
| 34.231 | 2.6173 | 1.5 |
| 34.92 | 2.5673 | 2.4 |
| 35.637 | 2.5172 | 3 |
| 36.041 | 2.4899 | 2.7 |
| 36.616 | 2.4522 | 2.6 |
| 37.021 | 2.4263 | 2.1 |
| 37.617 | 2.3891 | 1.9 |
| 39.6 | 2.274 | 4.1 |
| 40.461 | 2.2275 | 1.4 |
| 40.847 | 2.2074 | 1.7 |
| 42.4 | 2.13 | 1.3 |
| 43.137 | 2.0953 | 1.4 |
| 43.96 | 2.058 | 1.1 |
| 44.201 | 2.0474 | 1.1 |

Example 2

Slurry or dissolve 50 mg of N-(4-fluorobenzyl)-N-(1-methylpiperidin-4-yl)-N'-[4-(2-methylpropoxy)phenylmethyl]urea in 0.5 mL ethanol, and then add tartaric acid at three times the molar equivalent of N-(4-fluorobenzyl)-N-(1-methylpiperidin-4-yl)-N'-[4-(2-methylpropoxy)phenylmethyl]urea to produce a precipitate. The precipitation was allowed to be stirred overnight and the N-(4-fluorobenzyl)-N-(1-methylpiperidin-4-yl)-N'-[4-(2-methylpropoxy)phenylmethyl]urea tartrate was obtained.

Example 3

Slurry 50 mg of N-(4-fluorobenzyl)-N-(1-methylpiperidin-4-yl)-N'-[4-(2-ethylpropoxy)phenylmethyl]urea in 0.5 mL n-propanol, and then add tartaric acid at three times the molar equivalent of N-(4-fluorobenzyl)-N-(1-methylpiperidin-4-yl)-N'-[4-(2-methylpropoxy)phenylmethyl]urea to produce a precipitate. The precipitation was allowed to be stirred overnight and the N-(4-fluorobenzyl)-N-(1-methylpiperidin-4-yl)-N'-[4-(2-methylpropoxy)phenylmethyl]urea tartrate was obtained.

In the present invention, the N-(4-fluorobenzyl)-N-(1-methylpiperidin-4-yl)-N'-[4-(2-methylpropoxy)phenylmethyl]urea tartrate form III, the XRPD patterns is shown in FIG. 1 and the diffraction peaks of the XRPD pattern of Form III are listed in the following table:

| 2-Theta | d(Å) | I(Height)% |
|---|---|---|
| 5.359 | 16.4771 | 2 |
| 6.76 | 13.065 | 38.7 |
| 8.64 | 10.2261 | 2.7 |
| 9.62 | 9.1861 | 9.4 |
| 11.386 | 7.7649 | 1.1 |
| 12.999 | 6.8048 | 6.8 |
| 13.319 | 6.6424 | 10 |
| 14.162 | 6.2485 | 12.1 |
| 14.498 | 6.1043 | 59.1 |
| 15.279 | 5.7942 | 9.7 |
| 15.9 | 5.5693 | 1.4 |
| 16.124 | 5.4925 | 2.3 |
| 16.458 | 5.3817 | 3.8 |
| 17.342 | 5.1093 | 7.4 |
| 17.96 | 4.9347 | 7.6 |
| 18.655 | 4.7525 | 8.4 |
| 19.461 | 4.5575 | 29.2 |
| 19.919 | 4.4537 | 100 |
| 20.418 | 4.3459 | 1.8 |
| 21.039 | 4.219 | 5.3 |
| 21.656 | 4.1002 | 23.3 |
| 22.039 | 4.0298 | 7.9 |
| 22.579 | 3.9348 | 24.3 |
| 22.998 | 3.8639 | 3.2 |
| 23.619 | 3.7638 | 25.1 |
| 24.28 | 3.6627 | 16.5 |
| 25.656 | 3.4693 | 3.5 |
| 26.078 | 3.4141 | 6.3 |
| 26.538 | 3.356 | 3 |
| 27.018 | 3.2974 | 3.6 |
| 27.398 | 3.2525 | 2 |
| 27.801 | 3.2064 | 4.1 |
| 28.441 | 3.1356 | 10.9 |
| 28.721 | 3.1057 | 6.8 |
| 29.161 | 3.0598 | 6.5 |
| 30 | 2.9761 | 3.5 |
| 30.799 | 2.9007 | 8.1 |
| 31.139 | 2.8698 | 4.4 |
| 32.241 | 2.7742 | 3.6 |
| 32.7 | 2.7363 | 6.8 |
| 33.238 | 2.6932 | 3.4 |
| 34.231 | 2.6173 | 1.5 |
| 34.92 | 2.5673 | 2.4 |
| 35.637 | 2.5172 | 3 |
| 36.041 | 2.4899 | 2.7 |
| 36.616 | 2.4522 | 2.6 |
| 37.021 | 2.4263 | 2.1 |
| 37.617 | 2.3891 | 1.9 |
| 39.6 | 2.274 | 4.1 |
| 40.461 | 2.2275 | 1.4 |
| 40.847 | 2.2074 | 1.7 |
| 42.4 | 2.13 | 1.3 |
| 43.137 | 2.0953 | 1.4 |
| 43.96 | 2.058 | 1.1 |
| 44.201 | 2.0474 | 1.1 |

Example 4

Slurry 500 g of N-(4-fluorobenzyl)-N-(1-methylpiperidin-4-yl)-N'-[4-(2-ethylpropoxy)phenylmethyl]urea in 5 L 2-butyl alcohol, and then add tartaric acid at three times the molar equivalent of N-(4-fluorobenzyl)-N-(1-methylpiperidin-4-yl)-N'-[4-(2-methylpropoxy)phenylmethyl]urea to produce a precipitate. The precipitation was allowed to be stirred overnight and the N-(4-fluorobenzyl)-N-(1-methylpiperidin-4-yl)-N'-[4-(2-methylpropoxy)phenylmethyl]urea tartrate was obtained.

In the present invention, the N-(4-fluorobenzyl)-N-(1-methylpiperidin-4-yl)-N'-[4-(2-methylpropoxy)phenylmethyl]urea tartrate form III, the XRPD patterns is shown in FIG. 1 and the diffraction peaks of the XRPD pattern of Form III are listed in the following table:

| 2-Theta | d(Å) | I(Height)% |
|---|---|---|
| 5.342 | 16.5305 | 2.1 |
| 6.74 | 13.1029 | 37.5 |
| 9.54 | 9.2632 | 9.9 |
| 10.659 | 8.2928 | 2 |
| 11.34 | 7.7967 | 1.5 |
| 12.901 | 6.8566 | 12.3 |
| 13.338 | 6.6325 | 5.5 |
| 14.381 | 6.1538 | 65 |
| 15.161 | 5.8392 | 12.2 |
| 16.059 | 5.5146 | 4.1 |
| 17.24 | 5.1393 | 6.7 |
| 17.86 | 4.9622 | 6.7 |
| 18.5 | 4.7919 | 8.8 |
| 19.38 | 4.5764 | 51.2 |
| 19.82 | 4.4757 | 100 |
| 20.358 | 4.3587 | 2.3 |
| 20.918 | 4.2432 | 4.2 |
| 21.501 | 4.1295 | 24.2 |
| 21.902 | 4.0547 | 6.9 |
| 22.46 | 3.9553 | 22 |
| 23.481 | 3.7855 | 22.1 |
| 24.161 | 3.6804 | 27 |
| 24.663 | 3.6067 | 3.2 |
| 25.503 | 3.4898 | 3 |
| 25.939 | 3.4321 | 6.2 |
| 26.86 | 3.3165 | 4 |
| 27.241 | 3.271 | 2.7 |
| 27.7 | 3.2178 | 4.3 |
| 28.301 | 3.1509 | 14 |
| 28.639 | 3.1144 | 7.1 |
| 29.12 | 3.064 | 7.3 |
| 29.857 | 2.99 | 4.3 |
| 30.621 | 2.9172 | 8 |
| 31.017 | 2.8808 | 4.1 |
| 32.139 | 2.7828 | 4.3 |
| 32.521 | 2.7509 | 6.9 |
| 33.102 | 2.704 | 5.8 |
| 33.959 | 2.6377 | 1.3 |
| 34.398 | 2.605 | 1.5 |
| 34.701 | 2.583 | 2.1 |
| 35.401 | 2.5334 | 2.4 |
| 35.857 | 2.5023 | 1.3 |
| 36.418 | 2.465 | 2.9 |
| 36.88 | 2.4352 | 1.6 |
| 37.383 | 2.4036 | 2.9 |
| 38.275 | 2.3496 | 1.3 |
| 39.399 | 2.2851 | 5.5 |
| 40.243 | 2.2391 | 1.7 |
| 41.03 | 2.1979 | 0.9 |
| 42.239 | 2.1378 | 1.5 |
| 42.977 | 2.1028 | 2.1 |

Example 5

Powder fluidity test: the tray is a 7 cm diameter petri dish. The two glass funnels are overlapped on the iron frame. The distance between the lower funnel outlet and the Petri dish is 3.5-6.0 cm. Pimavanserin tartrate salt was added slowly from the upper funnel, and the sample was gradually accumulated on the petri dish through the buffer of the two funnels to form a cone until the highest cone was obtained. Determine the height H of the cone, measure each sample three times, take the average value, and calculate the angle of repose according to the following formula:

$$\alpha = \arctan(H/R)$$

where α is the angle of repose and R is the radius of the dish

When the angle of repose of the powder is less than or equal to 30 degrees, it means the flowability of this powder is good. While in case, 40 degrees or less of the powder angle of repose, this powder can satisfy the demand for fluidity in the production process. When the angle of repose of the powder is more than 40 degrees, it means the very poor flowability of the drug powder which may cause the troubles above mentioned during the drug manufacturing process.

| Pimavanserin tartrate Crystal forms | Source of Pimavanserin tartrate Crystal forms | angle of repose |
|---|---|---|
| Form A | Prepared according to CN101035759 B Example 5 | 45° |
| Form B | Prepared according to CN101035759 B Example 15 | 43° |
| Form C | Prepared according to CN101035759 B Example 33 | 41° |
| Form III | Present invention Example 4 | 32° |

Compared to existing Pimavanserin tartrate Form A, B, and C, Form III significantly improves the powder flowability, which is more suitable for formulation process and pimavanserin formulation manufacturing.

The invention claimed is:

1. A crystal form III of N-(4-fluorobenzyl)-N-(1-methylpiperidin-4-yl)-N'-[4-(2-methylpropoxy)phenylmethyl]urea hemi-tartrate, having an X-ray powder diffraction pattern, comprising diffraction peaks at at least 2θ value of: 14.6±0.2, 19.5±0.2, 6.9±0.2, 20.0±0.2, and 24.4±0.2.

2. The crystal form HI of claim 1, wherein the X-ray powder diffraction pattern further comprises diffraction peaks at at least one 2θ value of: 19.1±0.2, 5.2±0.2, 15.3±0.2, 28.5±0.2, 13.1±0.2, or 9.7±0.2.

3. The crystal form III of claim 1, wherein the X-ray powder diffraction pattern further comprises diffraction peaks at at least one 2θ value of: 9.0±0.2, 5.6±0.2, 29.4±0.2, 23.7±0.2, 25.0±0.2, or 26.3±0.2.

4. The crystal form HI of claim 1, wherein the X-ray powder diffraction pattern further comprises diffraction peaks at at least one 2θ value of: 32.6±0.2, 8.3±0.2, 16.7±0.2, 33.3±0.2, 36.6±0.2, or 30.8±0.2.

5. The crystal form III of claim 1, wherein the X-ray powder diffraction pattern further comprises diffraction peaks at at least one 2θ value of: 39.6±0.2, 16.2±0.2, 37.6±0.2, 10.9±0.2, 27.5±0.2, or 37.0±0.2.

6. A pharmaceutical composition comprising the N-(4-fluorobenzyl)-N-(1-methylpiperidin-4-yl)-N'-[4-(2-ethylpropoxy)phenylmethyl]urea hemi-tartrate crystal form III according to claim 1 as an active ingredient.

7. A process for the preparation of N-(4-fluorobenzyl)-N-(1-methylpiperidin-4-yl)-N'-[4-(2-methylpropoxy)phenylmethyl]urea hemi-tartrate crystal form III according to claim 1, comprising:
  (i) dissolving N-(4-fluorobenzyl)-N-(1-methylpiperidin-4-yl)-N'-[4-(2-methylpropoxy)phenylmethyl]urea in an organic solution;
  (ii) adding tartaric acid at three times the molar amount of the N-(4-fluorobenzyl)-N-(1-methylpiperidin-4-yl)-N'-[4-(2-methylpropoxy)phenylmethyl]urea into the solution prepared in the step (i) to precipitate a N-(4-fluorobenzyl)-N-(1-methylpiperidin-4-yl)-N'-[4-(2-methylpropoxy)phenylmethyl]urea hemi-tartrate salt; and
  (iii) obtaining N-(4-fluorobenzyl)-N-(1-methylpiperidin-4-yl)-N'-[4-(2-methylpropoxy)phenylmethyl]urea hemi-tartrate crystal form III after liquid-solid separation.

8. A method of treating a dopamine receptor-related disease in a subject, the method comprising: administering to the subject a pharmaceutical composition including an effective amount of N-(4-fluorobenzyl)-N-(1-methylpiperidin-4-yl)-N'-[4-(2-methylpropoxy)phenylmethyl]urea hemi-tartrate crystal form III according to claim 1, wherein the dopamine receptor-related disease includes mental illness, neurodegenerative diseases, dyskinesia, dystonia or thrombosis.

9. The method of claim 8, wherein the dopamine receptor-related disease includes psychosis, schizophrenia, schizoaffective disorder, mania, psychotic depression, affective disorder, dementia, anxiety, sleep disorder, appetite disorder, bipolar disorder, psychosis secondary to hypertension, migraine, vasospasm and ischemia, motor convulsions, tremors, psychomotor retardation, bradykinesia and psychotic pain, Parkinson's disease, Huntington's disease, Alzheimer's disease, spinocerebellar atrophy, Tourette Syndrome, Friedreich Ataxia, Machado-Joseph disease, Lewy body dementia, progressive supranuclear palsy and frontotemporal dementia, myoclonus, tremor, myocardial infarction, thrombosis Sexual or ischemic stroke, idiopathic and thrombotic thrombocytopenic purpura, peripheral vascular disease, or Raynaud's disease.

* * * * *